United States Patent [19]

Stückler

[11] 4,126,636
[45] Nov. 21, 1978

[54] PROCESS OF PRODUCING THE MAGNESIUM SALT OF p-CHLOROPHENOXYISOLBUTYRIC ACID

[75] Inventor: Franz Stückler, Wolfsberg, Austria

[73] Assignee: Paul Hauser - Chepharin, chemisch-pharmazeutische Industriegesellschaft in Klagenfurt, Kärnten, Austria

[21] Appl. No.: 841,835

[22] Filed: Oct. 13, 1977

[30] Foreign Application Priority Data

Oct. 18, 1976 [AT] Austria .............................. 157751/76

[51] Int. Cl.² ............................................. C07C 65/08
[52] U.S. Cl. .................................................... 562/472

[58] Field of Search ..................................... 260/520 C

[56] References Cited

FOREIGN PATENT DOCUMENTS

2,356,655  5/1974  Fed. Rep. of Germany ....... 260/520 C

Primary Examiner—Paul J. Killos
Attorney, Agent, or Firm—Martin A. Farber

[57] ABSTRACT

P-chlorophenoxyisobutyric acid is dissolved in an aqueous solution of a surplus of ammonia. The resulting solution is reacted with an aqueous solution of a magnesium salt, which latter solution contains a large surplus of ammonium ions and gaseous ammonia.

4 Claims, No Drawings

PROCESS OF PRODUCING THE MAGNESIUM SALT OF p-CHLOROPHENOXYISOBUTYRIC ACID

This invention relates to a process of producing the magnesium salt of p-chlorophenoxyisobutyric acid having the formula

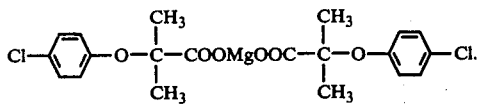

The magnesium salt of p-chlorophenoxyisobutyric acid is known, e.g., from Austrian Patent Specification No. 265,243 and German Opened Specification No. 2,308,331. In Austrian Patent Specification No. 265,243 it is proposed to produce the magnesium salt of p-chlorophenoxyisobutyric acid in that a magnesium compound, e.g., the acetate, the basic carbonate or the hydroxide, is reacted with p-chlorophenoxyisobutyric acid in an aqueous medium. In Opened German Specification No. 2,308,331 it is similarly suggested to cause magnesium compounds, such as magnesium sulfate or magnesium chloride, to react with p-chlorophenoxyisobutyric acid in the presence of sodium hydroxide in that the magnesium salt is stirred into a solution which contains the sodium salt of p-chlorophenoxyisobutyric acid.

Both known processes have the disadvantage that inexpensive magnesium compounds, such as magnesia, magnesium hydroxide and basic magnesium carbonate, are virtually insoluble in water so that only a slow reaction can be effected in an aqueous medium as the reaction takes place in a heterogeneous medium.

Another disadvantage of the known processes resides in that p-chlorophenoxyisobutyric acid must be transformed to its sodium salt. This is very difficult in practice because it is not simple to adjust exactly equivalent conditions for this neutralizing reaction. Magnesium salts must then be added also in an exactly equivalent quantity in order to avoid a surplus or deficiency of extraneous ions. For instance, in the process described in Opened German Specification No. 2,308,331, magnesium salt must be gradually added with stirring, and the acid and sodium hydroxide must be present in exactly stoichiometric proportions because any surplus sodium hydroxide would immediately cause the precipitation of the fed magnesium as magnesium hydroxide. In the known process it is highly expensive to separate the desired magnesium salt of p-chlorophenoxyisobutyric acid from the extraneous ions and the resulting product must be very thoroughly washed. It is apparent that the known processes are highly expensive and must be very exactly controlled. For these reasons, they have not been successful in practice.

The magnesium salt of p-chlorophenoxyisobutyric acid is a compound which is highly interesting for pharmaceutical purposes and which is superior in hypolipemic properties to the known other preparations based on p-chlorophenoxyisobutyric acid. The magnesium compound of p-chlorophenoxyisobutyric acid is superior to the free acid or the ethyl ester in use because it has improved compatibility after oral administration. Besides, magnesium is an essential component of tissues and body fluids and is of high physiological significance. The physiological significance of magnesium ions becomes apparent, e.g., in numerous metabolic reactions because the activity of the enzymes depends on certain ions. When magnesium ions are supplied in the form of the magnesium compound of p-chlorophenoxyisobutyric acid to the organism which suffers from hyperlipidemia, these magnesium ions very considerably increase the activity of p-chlorophenoxyisobutyric acid. When an increased decomposition of the lipoproteides present in the circulatory system has been initiated by p-chlorophenoxyisobutyric acid, that decomposition is promoted by the presence of magnesium or magnesium ions and this presence does not adversely affect the inhibiting activity of p-chlorophenoxyisobutyric acid on the hepatic biosynthesis of cholesterin during the conversion of acetyl-coenzyme A to mevalonic acid and on the synthesis of fatty acid at the rate-controlling stage by an inhibition of the acetyl-coenzyme A-carboxylase.

It is apparent that there is a considerable desire for a process which enables a simple production of the magnesium salt of p-chlorophenoxyisobutyric acid in high yields from substances which can be commercially mass-produced.

This object is accomplished according to the invention by the provision of a process in which p-chlorophenoxyisobutyric acid having the formula

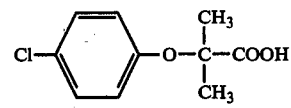

or a salt of such acid is dissolved in an aqueous solution of a surplus of ammonia and the resulting solution is mixed with an aqueous solution of a magnesium-ammonium salt solution. The dissolving of magnesia, magnesium hydroxide or basic magnesium carbonate in a solution of a surplus of an ammonium salt results in an aqueous solution of a magnesium salt, preferably magnesium chloride, and that aqueous solution contains, in accordance with the invention, a large surplus of ammonium ions and gaseous ammonia.

The reaction in an aqueous medium in the presence of ammonium ions and gaseous ammonia ensures that the magnesium compounds which are used will be in solution even under alkaline conditions so that the reaction is effected in a homogeneous medium. Besides, an exact control of the quantities in which the starting compounds are used is no longer required because both starting compounds are in solution and the presence of ammonium ions and gaseous ammonia causes the magnesium salt of p-chlorophenoxyisobutyric acid to precipitate as a crystalline substance of very high purity and even the use of a surplus of the magnesium compound is by no means disturbing. In the process according to the invention, the reaction takes place in a homogeneous medium so that there can be no phase boundary transitions which could adversely affect the yield.

A further advantage resides in that the ammonium salt-containing solution which is available after the separation of the desired magnesium salt can be re-used so that there are virtually no losses of ammonium salt.

The reactive derivatives of p-chlorophenoxyisobutyric acid which may be used include the salts of the acid, e.g., the sodium or ammonium salt.

The magnesium compounds which can be used include mainly magnesia, magnesium hydroxide and basic magnesium carbonate, although magnesium salts of organic acids, such as magnesium acetate or alcoholates, e.g., magnesium ethylate or the like, may also be used with good success. Because the process according to the invention permits of a use of magnesium compounds which are insoluble or only difficultly soluble in pure water, it is possible to use magnesium compounds, such as magnesia, magnesium hydroxide or basic magnesium carbonate, in which magnesium is available at lower cost than in the magnesium compounds mentioned in Opened German Specification No. 2,308,331. For instance, magnesia contains 60% by weight of magnesium, i.e. a higher percentage of magnesium than all other magnesium compounds.

Some examples of the process according to the invention will now be described:

EXAMPLE 1

34 g (about 0.6 mole) ammonium chloride were dissolved in 100 g demineralized water with stirring. 4.4 g (0.11 mole) magnesia was stirred into the resulting solution, which was heated to the boil with reflux cooling for 30 minutes. This resulted in the formation of a solution with release of ammonia gas. The solution was filtered.

20 g demineralized water was added to 42.9 g (0.20 mole) p-chlorophenoxyisobutyric acid. The addition of 22 g concentrated aqueous ammonia solution (24 to 26% concentration) with stirring resulted in a clear solution.

When the magnesium-containing solution was stirred into the acid-containing solution, the magnesium salt of p-chlorophenoxyisobutyric acid immediately began to settle as an initially resinous substance, which rapidly crystallized when stirred. The resulting mixture was placed into a refrigerator to complete the crystallization. 47.8 g of moist crystals, which smelled of ammonia, were recovered when the liquid was sucked off and were dried at 120° C. for 14 hours. The resulting product consisted of the purely white magnesium salt of p-chlorophenoxyisobutyric acid, melting point 318°–321° C., which is obtained in a yield of virtually 100%.

EXAMPLE 2

34 g (about 0.6 mole) ammonium chloride were dissolved in 100 g demineralized water and 4 g (0.1 mole) magnesia was stirred into the solution. The resulting mixture was boiled with reflux cooling for 30 minutes until a clear solution was available, which was filtered when cold.

60 g demineralized water were added to 43 g (about 0.2 mole) p-chlorophenoxyisobutyric acid and 26 g concentrated aqueous ammonia solution (24 to 26% concentration) were added. The resulting mixture was stirred until the soluble substances had been completely dissolved. The solution was filtered too.

When the magnesium-containing solution was stirred into the acid-containing solution, a paste was formed and this was immediately succeeded by the crystallization of the magnesium salt. To complete the crystallization, the reaction mixture was kept in a refrigerator over night. Liquid was sucked from the crystals. When they had been dried at 60° for 6 hours, 49 g of the tetrahydrate of the magnesium salt of p-chlorophenoxyisobutyric acid, melting point above 300° C., were obtained. When the tetrahydrate was subsequently dried at 120° C. for 15 hours, 42 g of the anhydrous magnesium salt of p-chlorophenoxyisobutyric acid (yield 93%), melting point 320°–322° C., were obtained.

EXAMPLE 3

40 g ammonium chloride were dissolved in 100 g demineralized water with gentle heating. 4.4 g (0.11 mole) magnesia were stirred into the resulting solution. When the resulting mixture was heated to the boil with reflux cooling for 15 minutes, ammonia gas was released and a slightly turbid solution was obtained. When the solution was filtered, a clear filtrate became available.

42.9 g (0.20 mole) p-chlorophenoxyisobutyric acid and 20 g demineralized water were stirred together. 20 g aqueous concentrated ammonia solution (24 to 26% concentration) were then stirred in. The magnesium-containing solution was stirred into the resulting solution so that the latter became turbid and a resinous substance settled and subsequently crystallized when stirred. The reaction mixture was kept in a refrigerator over night to complete the crystallization. Liquid was sucked and thoroughly pressed from the crystals. When the latter were dried, the weight was constant after about 2 hours. After the crystals had been dried for a total of 20 hours, 43.8 g of the magnesium salt of p-chlorophenoxyisobutyric acid (yield 97%) were obtained in the form of pale yellow crystals having a melting point of 318°–320° C.

EXAMPLE 4

40 g ammonium chloride were dissolved in 100 g demineralized water with gentle heating. 4.4 g (0.11 mole) magnesia were stirred into the resulting solution. When the resulting mixture was heated to the boil with reflux cooling for 15 minutes, a slightly turbid solution was obtained, which was then filtered.

42.9 g (0.20 mole) p-chlorophenoxyisobutyric acid were dissolved in 60 g aqueous ammonia solution (10% concentration) and the resulting solution was filtered. When the magnesium-containing solution made as described hereinbefore was stirred into the acid solution, the latter became turbid and a resinous substance settled, which crystallized when stirred. The reaction mixture was kept in a refrigerator over night. Thereafter, liquid was sucked and pressed from the crystals, which were subsequently washed with 15 ml demineralized water and then dried at 120° C. for 2 hours. 42.26 g of the magnesium salt of p-chlorophenoxyisobutyric acid (yield 93.6%) were obtained in the form of white crystals having a melting point of 322°–325° C.

EXAMPLE 5

50 g ammonium chloride were dissolved in 140 g demineralized water with heating. 4.4 g (0.11 mole) magnesium oxide were stirred into the resulting solution. When the resulting mixture was heated to the boil with reflux cooling for 30 minutes, ammonia gas was released and a yellowish solution was obtained, which was filtered. The filtrate was clear and colorless.

42.9 g (0.20 mole) p-chlorophenoxyisobutyric acid were dissolved in 60 g aqueous ammonia solution (10% concentration). The resulting solution was filtered.

When the magnesium-containing solution was heated to 80° C. and was then stirred into the acid-containing solution, crystals were precipitated immediately. The mixture was cooled to 20° C. and was stirred. Liquid was sucked and thoroughly pressed from the crystals, which were then dried at 120° C. for 1¼ hours. 44.64 g of the magnesium salt of p-chlorophenoxyisobutyric acid (98.8% yield) were obtained in the form of white crystals havng a melting point of 318°–322° C.

EXAMPLE 6

30 g (about 0.6 mole) ammonium chloride were dissolved in 140 g aqueous ammonia solution (10% concentration). 21 g (about 0.105 mole) magnesium chloride ($MgCl_2 \cdot 6H_2O$) were dissolved in the resulting solution with stirring. The resulting solution was filtered.

43 g (about 0.2 mole) p-chlorophenoxyisobutyric acid were charged into 60 g demineralized water. 26 g concentrated ammonia solution (24 to 26% concentration) were added to the mixture, which was stirred until all soluble matter had been dissolved. When the magnesium-chloride solution was stirred into the acid-containing solution, a paste was formed and the magnesium salt of p-chlorophenoxyisobutyric acid began to crystallize immediately. The reaction mixture was kept in a refrigerator over night to complete the crystallization. Liquid was then sucked from the precipitated crystals, which were subsequently dried for about 4 hours at 60°. 45 grams of the tetrahydrate of the magnesium salt of p-chlorophenoxyisobutyric acid were thus obtained. When the tetrahydrate was dried at 120° C. for 15 hours, 38.2 g anhydrous magnesium salt of p-chlorophenoxyisobutyric acid (yield 84.5%) having a melting point of 319°–322° C. were obtained.

EXAMPLE 7

35 g (about 0.65 mole) ammonium chloride were dissolved with stirring in 100 g demineralized water. 6.4 g (about 0.11 mole) magnesium hydroxide were stirred into the resulting solution. When the resulting mixture was heated to the boil with reflux cooling for 30 minutes, a colorless solution formed and ammonia gas was released. When the solution was filtered, a clear filtrate was obtained.

42.9 g (0.20 mole) p-chlorophenoxyisobutyric acid were dissolved in 60 g aqueous ammonia solution (10% concentration). The solution was filtered. When the magnesium-containing solution was stirred into the filtrate, the latter became turbid and a resinous substance separated, which crystallized when stirred. The reaction mixture was kept in a refrigerator over night to complete the crystallization. Liquid was then sucked and thoroughly pressed from the precipitated crystals. When the latter were dried at 120° C. for 23 hours, 45.2 g of the magnesium salt of p-chlorophenoxyisobutyric acid (yield 100%) were obtained in the form of white crystals having a melting point of 319° to 320° C.

This process results in a production of the magnesium salt of p-chlorophenoxyisobutyric acid in extremely high yields, which are close to and in some cases even as high as the theoretically possible yield. For this reason the process affords advantages as regards process technology and economy.

EXAMPLE 8

50 g ammonium chloride were dissolved in 140 g demineralized water with gentle heating. 11 g (about 0.11 mole) basic magnesium carbonate (light-weight powder Ph.Eur.I) were stirred into the resulting solution. When the resulting mixture was heated to the boil with reflux cooling for 1 hour, ammonia gas was released and a yellowish solution was obtained, which was filtered. The filtrate was colorless and clear.

42.9 (0.20 mole) p-chlorophenoxyisobutyric acid were dissolved in 60 g aqueous ammonia solution (10% concentration). The resulting solution was filtered. When the magnesium-containing solution, heated to 80° C., was stirred into the filtrate which contained the p-chlorophenoxyisobutyric acid, the magnesium, salt crystallized immediately. The reaction mixture was cooled to room temperature and thoroughly stirred and the liquid was then sucked from the crystals. When the latter were dried at 120° C. for 19 hours, 43.37 g of the magnesium salt of p-chlorophenoxyisobutyric acid (yield 96%) were obtained in the form of white crystals having a melting point of 316° to 319° C.

For instance, important advantages regarding process technology result from the reaction in the presence of ammonium ions and gaseous ammonia because the p-chlorophenoxyisobutyric acid is reacted in an ammonia solution which contains more ammonium ions than p-chlorophenoxyisobutyric acid.

What is claimed is:

1. A process of producing the magnesium salt of p-chlorophenoxyisobutyric acid having the formula

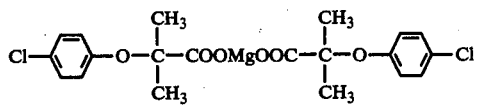

which comprises dissolving p-chlorophenoxyisobutyric acid having the formula

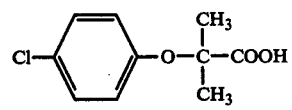

in an aqueous solution of a surplus of ammonia and reacting the resulting solution with an aqueous solution of a magnesium salt, which latter solution contains a surplus of ammonium ions and gaseous ammonia.

2. A process as set forth in claim 1, in which said magnesium salt is magnesium chloride.

3. A process as set forth in claim 1, in which said solutions are reacted with each other at elevated temperature.

4. A process as set forth in claim 1, in which said solutions are reacted with each other in the presence of a surplus of magnesium ions, whereby the magnesium salt of p-chlorophenoxyisobutyric acid is formed in an ammoniacal solution which contains unreacted magnesium ions.

* * * * *

UNITED STATES PATENT AND TRADEMARK OFFICE
CERTIFICATE OF CORRECTION

PATENT NO. : 4,126,636
DATED : November 21, 1978
INVENTOR(S) : Franz Stückler

It is certified that error appears in the above-identified patent and that said Letters Patent are hereby corrected as shown below:

Item [54] In the title the word "p-CHLOROPHENOXYISOLBUTYRIC" should be --p-CHLOROPHENOXYISOBUTYRIC--

Signed and Sealed this

Twentieth Day of February 1979

[SEAL]

Attest:

RUTH C. MASON
Attesting Officer

DONALD W. BANNER
Commissioner of Patents and Trademarks